United States Patent
Kishan et al.

(10) Patent No.: US 7,321,069 B2
(45) Date of Patent: Jan. 22, 2008

(54) PROCESS FOR PREPARING BISPHENOLS

(75) Inventors: Gurram Kishan, Bangalore (IN); Ramesh Krishnamurti, Bangalore (IN); Kapila Debjani, Bangalore (IN); Arakali Radhakrishna Srinivasarao, Bangalore (IN); Jan-Pleun Lens, Breda (NL)

(73) Assignee: General Electric Company, Schenectady, NY (US)

( * ) Notice: Subject to any disclaimer, the term of this patent is extended or adjusted under 35 U.S.C. 154(b) by 347 days.

(21) Appl. No.: 11/015,183

(22) Filed: Dec. 17, 2004

(65) Prior Publication Data

US 2006/0135825 A1    Jun. 22, 2006

(51) Int. Cl.
   *C07C 39/12*    (2006.01)
(52) U.S. Cl. ..................................... 568/727
(58) Field of Classification Search ............... 568/727
   See application file for complete search history.

(56) References Cited

U.S. PATENT DOCUMENTS

| | | | | |
|---|---|---|---|---|
| 4,777,301 A | * | 10/1988 | Olson | 568/727 |
| 5,169,992 A | * | 12/1992 | Knifton | 568/727 |
| 5,304,688 A | * | 4/1994 | Bowman et al. | 568/727 |
| 5,463,140 A | | 10/1995 | Wehmeyer et al. | |
| 5,631,338 A | * | 5/1997 | Inoue et al. | 528/30 |
| 5,939,494 A | | 8/1999 | Wehmeyer et al. | |
| 6,051,658 A | | 4/2000 | Wehmeyer et al. | |
| 6,133,190 A | | 10/2000 | Wehmeyer et al. | |
| 6,465,697 B1 | * | 10/2002 | Palmer et al. | 568/728 |
| 6,534,686 B1 | | 3/2003 | Webb et al. | |
| 6,620,939 B2 | | 9/2003 | Webb et al. | |

FOREIGN PATENT DOCUMENTS

| | | |
|---|---|---|
| EP | 0566798 | 10/1993 |
| JP | 2045439 | 2/1990 |
| JP | 5310624 | 11/1993 |
| JP | 8198791 | 6/1996 |
| JP | 10017509 | 1/1998 |
| JP | 2000160143 A2 * | 6/2000 |
| JP | 20001601432 A2 * | 6/2000 |
| WO | 0039059 | 7/2000 |

OTHER PUBLICATIONS

JP05310624; Nov. 22, 1993; Abstract Only (2 pgs).
JP04145039; May 19, 1992; Abstract Only (1 pg).
JP07003002; Jan. 6, 1995; (1 pg).

* cited by examiner

*Primary Examiner*—Shailendra Kumar
*Assistant Examiner*—Jennifer Cho

(57) ABSTRACT

A process for preparing aromatic bisphenols, wherein the method comprises reacting an aromatic hydroxy compound with an alkylating agent having a functionality of two in the presence of a catalyst system. The catalyst system used for the process is selected from the group consisting of a heteropolyacid compound, a clay, a functionalized metal oxide catalyst and combinations of the foregoing.

39 Claims, No Drawings

PROCESS FOR PREPARING BISPHENOLS

BACKGROUND

The disclosure generally relates to aromatic bisphenols prepared using a catalyst system. More particularly, the disclosure relates to aromatic bisphenols prepared using heteropolyacid catalysts, clays and functionalized metal oxide catalysts.

Bisphenols are valuable raw materials for producing polycarbonates. Polycarbonates are widely used in a variety of applications by virtue of their excellent physical properties, such as impact resistance, mechanical characteristics, transparency, and the like. Bisphenols are generally obtained by the reaction of a carbonyl compound with a phenol in the presence of an acidic catalyst, such as mineral acids or acidic ion exchange resins. One example of such acidic ion exchange resins is a sulfonated polystyrene resin cross-linked with divinylbenzene in the hydrogen form, (PS-DVB). Frequently, a co-catalyst is used in conjunction with the acidic catalyst, to improve the selectivity for bisphenol such as the para, para-bisphenol isomer, for example. Co-catalysts may be present as unattached molecules in the bulk reaction matrix, i.e., "bulk co-catalysts", or may be attached to the acidic resin catalyst through ionic or covalent linkages. Mercaptans are one class of co-catalysts that may be employed. More specifically, thiols, e.g., organosulfur compounds derived from hydrogen sulfide, are used as co-catalysts. Numerous efforts have been made to improve the selectivity for bisphenols by varying the mercaptan co-catalyst and the acidic catalyst. One approach that has been attempted is to use a catalyst having an attached co-catalyst, which is prepared, for example, by reacting a portion of the acidic groups of the acidic ion exchange resins with amino-mercaptans, to provide catalysts containing both mercaptan and sulfonic acid groups.

When ion exchange resin catalysts are used for making bisphenols by reaction of phenols with carbonyl compounds, the lifetime of the catalyst is affected by numerous factors, such as, for example, mechanical strength and fouling tendency. In addition, ion exchange resin catalysts typically require a pre-conditioning step, especially in continuous processes. Pre-conditioning is generally performed by passing the phenol through a packed bed of the ion exchange resin catalyst.

There remains a need in the art for alternative catalysts for preparing bisphenols that have superior mechanical properties, compressibility, non-swelling nature and hydrothermal stability as compared to the traditionally used ion-exchange resin catalysts, thereby leading to improved catalyst lifetime and/or productivity and bisphenol productivity.

BRIEF SUMMARY

Disclosed herein is a process for preparing aromatic bisphenols, wherein the process comprises reacting an aromatic hydroxy compound with an alkylating agent having a functionality of two, in the presence of a catalyst system. The catalyst system is selected from the group consisting of a heteropolyacid compound, a clay, a functionalized metal oxide catalyst and combinations of the foregoing. The alkylating agent having a functionality of two comprises a carbonyl compound of formula (I):

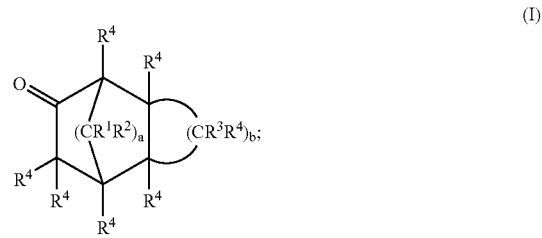

wherein $R^1$ to $R^4$ independently at each occurrence represent a hydrogen or an aliphatic radical and "a" and "b" are integers independently having values from 0 to 3.

In one embodiment, a process for preparing aromatic bisphenols comprises reacting an aromatic hydroxy compound with an alkylating agent having a functionality of two, in the presence of a catalyst system. The catalyst system comprises a functionalized metal oxide catalyst. The alkylating agent having a functionality of two comprises at least one functional group selected from the group consisting of a cyclopropyl ring, a cyclobutyl ring, an ethylenic group, an aliphatic hydroxy group, and a cycloaliphatic hydroxy group.

In one embodiment, a process for preparing 1,1-bis(3-methyl-4-hyxdroyxphenyl)cyclohexane comprises reacting cyclohexanone with ortho-cresol in the presence of a catalyst system. The catalyst system is selected from the group consisting of a heteropolyacid compound, a clay and a functionalized metal oxide catalyst and combinations of the foregoing.

In one other embodiment, a process for preparing 1,3-bis-4-hydroxyphenylmenthane comprises reacting terpene compound with phenol in the presence of a catalyst system. The catalyst system comprises a functionalized metal oxide catalyst.

DETAILED DESCRIPTION

The present disclosure may be understood more readily by reference to the following detailed description of preferred embodiments of the disclosure and the examples included therein. In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

The modifier "about" used in connection with a quantity is inclusive of the stated value and has the meaning dictated by the context (e.g., includes the degree of error associated with measurement of the particular quantity).

As used herein the term "consisting essentially of" as applied to the functionalized metal oxide catalyst means that the catalyst may have other components in which do not alter their catalytic, behavior.

As used herein the term "aliphatic radical" refers to a radical having a valence of at least one comprising a linear or branched array of atoms, which is not cyclic. The array may include heteroatoms such as nitrogen, oxygen, sulfur, silicon, and phosphorous or may be composed exclusively of carbon and hydrogen. Examples of aliphatic radicals include methyl, methylene, ethyl, ethylene, hexyl, n-propyl, isopropyl, n-butyl, sec-butyl, tertiary-butyl, pentyl, neopentyl, hexyl, heptyl, octyl, nonyl, decyl, undecyl, dodecyl, hexamethylene, trifluoromethyl, trifluoroethyl, methoxy, ethyloxy, oxyethyleneoxy ($O(CH_2)_2O$), trimethylsilyl, mixtures thereof and the like. Aliphatic radicals may be substituted or unsubstituted and may comprise one or more substituents including amino groups, halogen atoms, cyano groups, nitro groups, hydroxyl groups, mercapto groups, $C_1$-$C_{10}$ alkyl groups, $C_1$-$C_{10}$ alkoxy groups, $C_1$-$C_{10}$ alkoxycarbonyl groups, $C_1$-$C_{10}$ alkylthio groups, $C_1$-$C_{10}$ alkylamino groups, and the like.

As used herein the term "aromatic radical" refers to a radical having a valence of at least one comprising at least one aromatic group. Examples of aromatic radicals include phenyl, pyridyl, furanyl, thienyl, naphthyl, biphenyl, pyrrolyl, phenyl, biphenylene and mixtures thereof. The term includes groups containing both aromatic and aliphatic and or cycloaliphatic components, for example a benzyl group or an indanyl group. Aromatic radicals may be substituted or unsubstituted and may comprise one or more heteroatoms including and/or substituents including amino groups, halogen atoms, cyano groups, nitro groups, hydroxyl groups, mercapto groups, $C_1$-$C_{10}$ alkyl groups, $C_1$-$C_{10}$ alkoxy groups, $C_1$-$C_{10}$ alkoxycarbonyl groups, $C_1$-$C_{10}$ alkylthio groups, $C_1$-$C_{10}$ alkylamino groups, mixtures thereof and the like.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. Cycloaliphatic radicals may be "substituted" or "unsubstituted". A substituted cycloaliphatic radical is defined as a cycloaliphatic radical, which comprises at least one substituent. A substituted cycloaliphatic radical may comprise as many substituents as there are positions available on the cycloaliphatic radical for substitution. Substituents that may be present on a cycloaliphatic radical include but are not limited to halogen atoms such as fluorine, chlorine, bromine, and iodine. Substituted cycloaliphatic radicals include trifluoromethylcyclohexyl, hexafluoroisopropylidenebis-(4-cyclohexyloxy) (i.e. —O $C_6H_{10}C(CF_3)_2 C_6H_{10}O$—), chloromethylcyclohexyl; 3-trifluorovinyl-2-cyclopropyl; 3-trichloromethylcyclohexyl (i.e. 3-$CCl_3C_6H_{10}$—), bromopropylcyclohexyl (i.e. $BrCH_2CH_2CH_2 C_6H_{10}$—), and the like. For convenience, the term "unsubstituted cycloaliphatic radical" is defined herein to encompass a wide range of functional groups. Examples of suitable cycloaliphatic radicals include cyclobutyl, cyclopentyl, cyclohexyl, methylcyclohexyl, cycloheptyl, 4-allyloxycyclohexyl, aminocyclohexyl (i.e., $H_2N C_6H_{10}$—), aminocarbonylcyclopentyl (i.e., $NH_2COC_5H_8$—), 4-acetyloxycyclohexyl, dicyanoisopropylidenebis(4-cyclohexyloxy) (i.e., —O $C_6H_{10}C(CN)_2 C_6H_{10}$—), 3-methylcyclohexyl, methylenebis(4-cyclohexyloxy) (i.e., —O $C_6H_{10}CH_2 C_6H_{10}O$—), ethylcyclobutyl, cyclopropylethenyl, 3-formyl-2-terahydrofuranyl, 2-hexyl-5-tetrahydrofuranyl; hexamethylene-1,6-bis(4-cyclohexyloxy) (i.e., —O $C_6H_{10} (CH_2)_6 C_6H_{10}O$—); 4-hydroxymethylcyclohexyl (i.e., 4-$HOCH_2 C_6H_{10}$—), 4-mercaptomethylcyclohexyl (i.e. 4-$HSCH_2 C_6H_{10}$—), 4-methylthiocyclohexyl (i.e., 4-$CH_3S C_6H_{10}$—), 4-methoxycyclohexyl, 2-methoxycarbonylcyclohexyloxy (2-$CH_3OCO C_6H_{10}O$—), nitromethylcyclohexyl (i.e., $NO_2CH_2C_6H_{10}$—), trimethylsilylcyclohexyl, t-butyldimethylsilylcyclopentyl, 4-trimethoxysilylethylcyclohexyl (i.e., $(CH_3O)_3SiCH_2CH_2C_6H_{10}$—), vinylcyclohexenyl, vinylidenebis(cyclohexyl), and the like. The term "a $C_3$-$C_{10}$ cycloaliphatic radical" includes substituted cycloaliphatic radicals and unsubstituted cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

In one embodiment, a method for preparing aromatic bisphenols includes reacting an aromatic hydroxy compound with an alkylating agent having a functionality of two, in the presence of a catalyst system. The catalyst system is selected from the group consisting of a heteropolyacid compound, a clay, a functionalized metal oxide catalyst and combinations of the foregoing. The alkylating agent having a functionality of two comprises a carbonyl compound of formula (I),

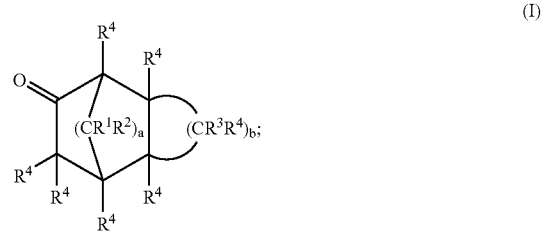

wherein $R^1$ to $R^4$ independently at each occurrence represent a hydrogen or an aliphatic radical and "a" and "b" are integers independently having values from 0 to 3. The alkylating agent having a functionality of two comprises at least one functional group selected from the group consisting of a cyclopropyl ring, a cyclobutyl ring, an ethylenic group, an aliphatic hydroxy group, and a cycloaliphatic hydroxy group.

In another embodiment, a process for preparing aromatic bisphenols comprises reacting an aromatic hydroxy compound with an alkylating agent having a functionality of two, in the presence of a catalyst system. The catalyst system comprises a functionalized metal oxide catalyst.

Suitable heteropolyacid compounds (hereinafter at times referred to as HPA) generally comprise a compound of formula (II),

wherein $M^1$ comprises hydrogen or an alkali metal such as lithium, sodium, potassium, rubidium, or cesium; $M^2$ comprises phosphorus or silicon, $M^3$ comprises tungsten or molybdenum and y is an integer having a value 0 to 10. In one embodiment, the heteropolyacid compound is selected from the group consisting of silicotungstic acid, silicomolybdic acid, phosphotungstic acid, and phosphomolybdic acid.

In another embodiment, the heteropolyacid compound is of formula (III):

wherein $M^4$ comprises a Group III element selected from the group consisting of boron, aluminum, gallium, and combinations of the foregoing Group III elements; $M^5$ comprises phosphorus or silicon, $M^6$ comprises tungsten or molybdenum and y is an integer having a value 0 to 10.

The heteropolyacids may be either unsupported or supported. Suitable supports for supported heteropolyacids are selected from the group consisting of silica (hereinafter at times referred to as $SiO_2$), alumina, niobia, metal oxides of Group III elements, metals oxides of Group IV elements, and transition metal oxides. Suitable Group III elements include boron, aluminum, gallium, cerium, and combinations of the foregoing Group III elements. Suitable Group IV elements include silicon, titanium, zirconium, and combinations of the foregoing Group IV elements Suitable clays are selected from the group consisting of

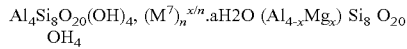

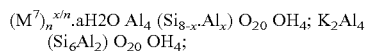

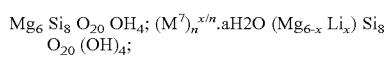

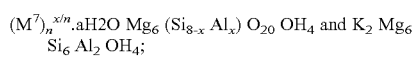

wherein $M^7$ represents an alkali metal or an alkaline earth metal cation, and a is an integer ranging from 0 to 10, x, y and n are integers ranging from 1 to 3. Non-limiting examples of the clay comprise pyrophillite, montmorillonite, beidellite, muscovite, talc, hectorite, saponite, and phlogopite. In one embodiment, $M^7$ is selected from the group consisting of sodium and lithium.

Suitable functionalized metal oxide catalysts comprise structural units of formulae (IV), (V), and (VI):

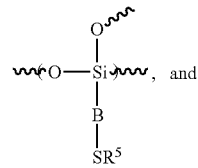

wherein $M^8$ comprises a metal oxide of a Group III element or a Group IV element or combinations of the foregoing, "B" and "C" independently comprise spacer groups selected from the group consisting of an aliphatic radical, a cycloaliphatic radical and an aromatic radical, and $R^5$ and $R^6$ independently comprise an alkali metal, a hydrogen, or an aliphatic radical. The Group III element is selected from the group consisting of boron, aluminum, gallium, cerium and combinations of the foregoing Group III elements. The Group IV element is selected from the group consisting of silicon, titanium, zirconium, and combination of the foregoing Group IV elements. In one embodiment, the Group III element is aluminum. In another embodiment, the Group IV element is zirconium.

The catalyst systems disclosed herein may be employed in conjunction with promoters. Suitable promoters may include mercaptans and a compound selected from the group consisting of hydroxy benzene and hydroxy naphthalene compounds.

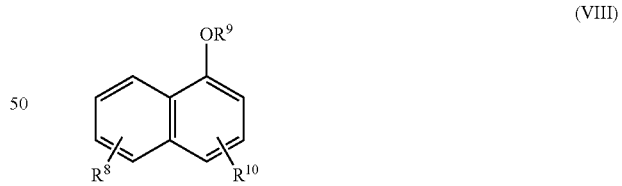

wherein $R^9$ and R8 are independently at each occurrence selected from the group consisting of a hydrogen or a $C_1$-$C_6$ aliphatic radical, $R^7$ is selected from the group consisting of an hydroxyl, —$OR^{11}$, and a $C_1$-$C_6$ aliphatic radical, c is an integer from 1 to 2; $R_{10}$ is selected from the group consisting of a hydrogen, an hydroxyl, —$OR^{11}$, and a $C_1$-$C_6$ aliphatic radical, wherein $R^{11}$ is a $C_1$-$C_6$ aliphatic radical.

Non-limiting examples of suitable mercaptan co-catalysts include 3-mercaptopropionic acid (hereinafter called 3-MPA), a substituted or an unsubstituted benzyl mercaptan, 3-mercapto-1-propanol, ethyl 3-mercaptopropionate, 1,4-bis (mercaptomethyl)benzene, 2-mercaptoethane-sulfonic acid, 3-mercaptopropanesulfonic acid, 4-mercaptobutanesulfonic acid, 4-mercaptopentane-sulfonic acid, 3-mercapto-2,2-dimethylpropanesulfonic acid, 2,3-dimercaptopropanesulfonic acid, mercaptopropane-2,3-disulfonic acid, 2-benzyl-4-mercaptobutanesulfonic acid, 5-mercaptopentanesulfonic acid, methanethiol, ethanethiol, isopropanethiol, butanethiol and mixtures of the foregoing mercaptan co-catalysts. In one embodiment, 3-mercaptopropionic acid is utilized because of its commercial availability and low cost, among others. Non-limiting examples of suitable hydroxy benzene and hydroxy naphthalene compounds include resorcinol, catechol, hytdroquionone, and the mono- and di-methyl and mono- and di-ethyl ethers thereof, para-ethylphenol, ortho-cresol, para-cresol, phloroglucinol, alpha-naphthol, 5-methyl-alpha-naphthol, 6-isobutyl-alpha-naphthol, 1,4-dihydroxynaphthalene, 6-hexyl-1,4-dihydroxy naphthalene and 6-methyl-4-methoxy-alpha-naphthalene.

In one embodiment, the alkylating agent having a functionality of two comprises a carbonyl compound of formula I:

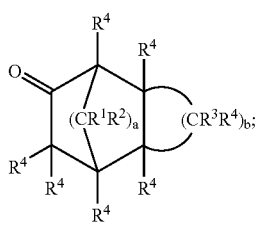

wherein $R^1$ to $R^4$ independently at each occurrence represent a hydrogen or an aliphatic radical, "a" and "b" are integers independently having values from 0 to 3; and $A^1$ is independently a divalent aromatic radical. In another embodiment, the alkylating agent having a functionality of two is a substituted or unsubstituted cyclohexanone selected from the group consisting of tricyclo[5.2.1.0$^{2,6}$] decanones, cyclohexanone, 4-perhydrocumyl cyclohexanone, 3,3,5-trimethylcyclohexanone and mixtures of the foregoing cycloalkanones. In one embodiment, the alkylating agent is cyclohexanone.

In another embodiment, the alkylating agent having a functionality of two comprises at least one functional group selected from the group consisting of a cyclopropyl ring, a cyclobutyl ring, an ethylenic group, an aliphatic hydroxy group, and a cycloaliphatic hydroxy group. In one embodiment, the alkylating agent comprises a terpene compound selected from the group consisting of alpha-terpinene, alpha-terpinol, alpha-pinene, limonene, gamma-terpinene, alpha-pinene, beta-pinene, sabinene, 2- carene, 3-carene and mixtures of the foregoing terpene compounds. In one embodiment the alkylating agent is limonene.

The aromatic hydroxy compound that may be used for producing the bisphenols may be a substituted or an unsubstituted aromatic compound containing at least one hydroxy group. Suitable aromatic hydroxy compounds include, but are not intended to be limited to, phenol, o-cresol, m-cresol, p-cresol, o- or m-cumenol, 2,6-dimethylphenol, 2-methyl-6-ethylphenol, 2-chlorophenol, 3-chlorophenol, 4-chlorophenol, 2-bromophenol, 2-tert-butylphenol, 2,4-dimethylphenol, 2-fluorophenol, 2,3,6-trimethylphenol, 2,3,5,6-tetramethylphenol, 2,6-dichlorophenol, 2,6-di-t-butylphenol, 2-phenylphenol, 2,6-diphenylphenol, 3,5-dimethylphenol, 3,5-diethylphenol, 2-benzylphenol, 2-ethyl-6-methylphenol, 2-phenoxyphenol, 3-methoxyphenol, 1-naphthol, 2-naphthol and mixtures of the foregoing aromatic hydroxy compounds.

In one embodiment, the aromatic bisphenols prepared by reacting a carbonyl compound with an aromatic hydroxy compound in the presence of the catalyst system comprise cycloalkylidene bisphenols of formula (IX).

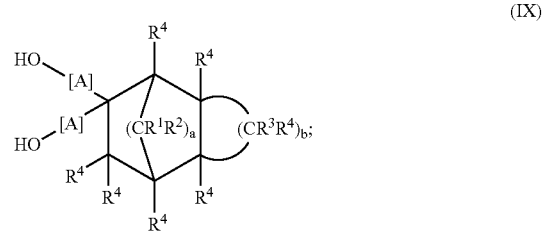

wherein $R^1$ to $R^4$, A, a and b have the same meaning as defined above. In one embodiment, o-cresol may be utilized for producing 1,1-bis(4-hydroxy-2-methylphenyl)cyclohexane (hereinafter referred to as DMBPC) by reaction with cyclohexanone in presence of functionalized catalyst system.

In one embodiment, the aromatic bisphenols prepared by reacting a terpene compound with an aromatic hydroxy compound in the presence of the functionalized metal oxide catalyst system comprises bisphenol structural units of formula (X):

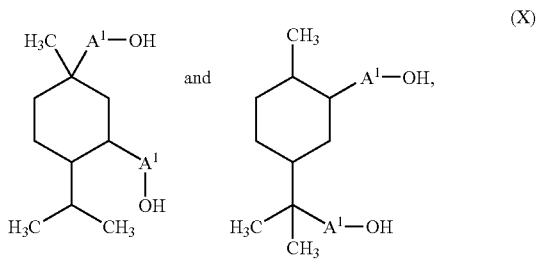

wherein $A^1$ is independently at each occurrence a divalent aromatic radical. In one embodiment, phenol may be utilized for producing 1,3- and 2,8-bis-4-hydroxyphenylmenthane (hereinafter at times referred to as BHPM) by reaction with limonene in presence of functionalized metal oxide catalyst.

In one embodiment, during the reaction of the alkylating agent having the functionality of two and the aromatic hydroxy compound in the presence of the catalyst system, the starting materials may isomerize to give other isomeric bisphenols. For example, as discussed above, in the reaction of phenol with limonene to form BHPM in the presence of a functionalized metal oxide catalyst, the reaction results in a mixture comprising 1,3-BHPM and 2,8-BHPM.

The catalyst systems disclosed herein may also be used in the preparation of bisphenols formed by reacting monofunctional alkylating agents with aromatic hydroxy compounds, such as, for example, the reaction of p-hydroxystyrene with phenol in presence of the catalyst system provides a bisphenol.

The process for forming the bisphenol compound in the presence of the catalyst system may be in either a batch mode or in a continuous mode. In the batch mode, the alkylating agent having a functionality of two and the aromatic hydroxy compound are preferably stirred in the presence of the catalyst. The progress of the reaction may be followed by numerous analytical techniques, such as gas chromatography or high-pressure liquid chromatography.

In the continuous process, the alkylating agent having a functionality of two and the aromatic hydroxy compound are continuously introduced into at least one reactor comprising a fixed bed of the catalyst or a fluidized bed packing of the catalyst. For example, the continuous process for making bisphenols may be carried out in a single reactor packed with the catalyst system, wherein the aromatic hydroxy compound is passed continuously into the reactor and the alkylating agent having a functionality of two is selectively introduced into one or more stages of the reactor. The staged addition of the alkylating agent having a functionality of two may provide improved bisphenol selectivity.

It should be noted that the catalyst system employed in the batch mode or continuous mode may be in a variety of forms such as, for example, a powder, pellets of any shape, a coating on the outside of an inert aggregate or bead formed of alumina, silica, and the like, a coating on the inside of a pipe reactor, or a monolithic structure.

The molar ratio of the aromatic hydroxy compound to the alkylating agent having the functionality of two in the presence of the catalyst is 2:1 to 40:1. More specifically, the molar ratio of the aromatic hydroxy compound to the alkylating agent having the functionality of two is 10:1 to 35:1. In one embodiment, the molar ratio is 20:1 to 30:1.

The amount of catalyst system used in the reaction of the alkylating agent having the functionality of two with an aromatic hydroxy compound is about 0.5 weight percent to about 10 weight percent of an overall weight of the reaction mixture. More specifically, the amount of catalyst used is about 1 weight percent to about 8 weight percent. In on embodiment, the amount of catalyst used is about 3 weight percent to about 5 weight percent. As used herein, the term "reaction mixture" refers to a mixture comprising a alkylating agent having a functionality of two and an aromatic hydroxy compound that is reacted in the presence of a catalyst system. As used herein, the term "overall weight of the reaction mixture" refers to the weight of a reaction mixture comprising a alkylating agent having a functionality of two and an aromatic hydroxy compound.

The feed stream containing the aromatic hydroxy compound and the alkylating agent having a functionality of two is preferably introduced to the catalyst system at a temperature of about 10° C. to about 200° C. Within this range, the initial temperature is specifically greater than or equal to about 30° C., more specifically greater than or equal to about 40° C., and even more specifically greater than or equal to about 45° C. The term initial temperature as used herein implies the temperature at which the aromatic hydroxy compound and the alkylating agent having a functionality of two are introduced to the catalyst system. In one embodiment, the reaction between the aromatic hydroxy compound and the alkylating agent having the functionality of two in the presence of the catalyst takes place at a reaction temperature of about 40° C. to about 120° C. Within this range, the reaction temperature is specifically greater than or equal to about 40° C., more specifically greater than or equal to about 80° C. and even more specifically greater than or equal to about 100° C. Passing the above noted feed stream through the catalyst produces an effluent containing bisphenol, residual starting materials, water produced as a by-product of the reaction, and other byproducts.

Once formed in the effluent, the bisphenol may then be isolated from the residual starting materials, water and byproducts by various techniques, such as for example, vacuum distillation. The removed alkylating agent having a functionality of two and residual aromatic hydroxy compound may be separated from the water, recovered, and then recycled to the reaction feed. The aromatic hydroxy compound removed from the product stream may be recycled for use in the catalyzed reaction or adduct crystallization, when present. Advantageously, the selectivity of the reaction for bisphenol results in the amount of impurities being reduced, thus facilitating the isolation of the bisphenol and improving the overall efficiency of the reaction.

Many catalysts that are used commercially do not exhibit very high selectivity if the feed stream comprises only aromatic hydroxy compound and alkylating agent having a functionality of two. A technique frequently used to achieve higher bisphenol selectivity is to use a feed stream comprising not only fresh aromatic hydroxy compound and alkylating agent having a functionality of two, but also a recycle stream comprising impurities generally produced in a previous alkylation reaction batch (or pass, for a continuous process). As used herein, the term "fresh aromatic hydroxy compound" means aromatic hydroxy compound that is newly added other than that contained in the recycle stream. This approach generally gives relatively higher overall bisphenol selectivity. In this case, the net selectivity may be improved by recycling impurities to the reactor to suppress isomerization reactions and/or further production of impurities. This enables simpler downstream isolation schemes because the purity of bisphenol in the reactor effluent is higher. The catalyst systems, therefore are capable of producing high bisphenol selectivity in general, under conditions where the reactor feed comprises substantial levels of impurity recycle to the reactor, as compared to the bisphenol selectivity expected with a virgin feed, that is, the feed does not comprise a substantial impurity recycle.

In other embodiments of the continuous process, a single or multiple reactor scheme that includes the fixed bed packing of the catalyst may further comprise packing structures designed to alleviate the hydraulic stress that generally results from prolonged operation. Such packing structures may assume a variety of structures specially designed to withstand hydraulic stress, and may comprise materials inert to the reactive materials used for producing bisphenols. For example, the packing structures may comprise materials, such as steel, aluminum, ceramic, and the like. The catalyst systems as disclosed herein are believed to have crushing strengths much higher than those reported for the traditionally used acidic ion exchange resin catalysts. Thus, the presence of the packing structures is expected to further improve the lifetime of the catalyst packing.

The catalyst systems described in this disclosure are useful for producing the above disclosed bisphenols in high yield and selectivity. Moreover, the use of catalyst systems offer improved mechanical strength and less fouling over prolonged periods of use, which results in longer catalyst lifetimes, thereby reducing operating costs.

Aromatic bisphenols of formulae (IX) and (X), may also be prepared by following methods described in co-pending U.S. patent application Ser. Nos. 10/675141 and 10/637761, incorporated herein by reference in their entireties.

Aromatic bisphenols prepared in accordance with the methods described herein are especially suitable for preparing polycarbonates. Polycarbonates are generally prepared by the polymerization reaction of an aromatic dihydroxy compound with a carbonate precursor, such as carbonyl halides or diaryl carbonates. Methods of polymerization include those disclosed in the art, such as interfacial polymerization, melt polymerization, solid-state polymerization, and solution polymerization. The bisphenols thus obtained are valuable for producing the polycarbonates compositions, which in turn are useful for making various articles useful for high heat, optical, and engineering applications.

Experimental Section

Analytical Method: Weight percent of the bisphenol was determined by standard high performance liquid chromatography technique (HPLC). BHPM was estimated by using the following technique. A standard solution of naphthalene in acetonitrile was prepared. Internal standard solutions containing 1,3-BHPM and 2,8-BHPM were prepared by diluting with the standard solution of naphthalene in acetonitrile. A sample of the reaction mixture was also diluted using the standard solution of naphthalene in acetonitrile. The sample containing the internal standard and the sample containing the reaction mixture was injected into a reverse phase Zorbax XDB, C18, 5µ, (4.6 mm×250 mm) column. The mobile phase, consisting of water:methanol:acetonitrile in a 34:14:52 relative ratio by volume was used to elute the sample at a flow rate of 1.0 milliliter/minute (ml/min).

DMBPC was estimated by using the following technique. Standard solutions of ortho-cresol and DMBPC in acetonitrile were prepared at different concentrations and were injected into a reverse phase Zorbax XDB, C18 5µ (4.6×150 mm) to get the response factors. A sample of the reaction mixture was diluted with acetonitrile and injected into the reverse phase Zorbax XDB, C18 5µ (4.6×150 mm). The mobile phase, consisting of 0.1% v/v acetic acid in water in one reservoir and 0.1% v/v acetic acid in acetonitrile in another reservoir, was used to elute the sample at a flow rate of 0.6 ml/min.

The clay catalyst used in the reactions was commercially purchased from Engelhard Company, and the heteropolyacid (HPA) catalyst was obtained from Sigma-Aldrich Company. The supports such as silicon dioxide, for example, for the heteropolyacids were also obtained from Sigma-Aldrich Company.

Examples 1-3. These examples illustrate the synthesis of a supported heteropolyacid (HPA) catalyst. Distilled water was taken in a polypropylene beaker and phosphotungstic acid was dissolved to provide a clear solution. Fumed silica was then added into this solution under constant stirring. This mixture was then poured into a petri dish and dried in the oven at 100° C. for about 15-16 hours. The mixture was then calcined at 250° C. for about 6 hours. The quantities of reactants and materials taken to prepare the various silica-supported HPA catalysts are shown in Table 1.

TABLE 1

| Example | Catalyst System | Phosphotungstic acid in grams | Distilled water in milliliters | Fumed Silica in grams |
|---|---|---|---|---|
| 1 | 10% HPA on SiO2 | 0.5 | 50 | 5 |
| 2 | 20% HPA on SiO2 | 1.0 | 50 | 5 |
| 3 | 40% HPA on SiO2 | 2.0 | 50 | 5 |

Examples 4-8. These examples illustrate a method for the synthesis of functionalized metal oxide catalysts.

The functionalization of metal oxide catalysts was carried out in two parts. The first part included the introduction of sulfonic acid groups (—$SO_3H$ groups) on the metal oxide catalyst and the second part included the introduction of mercaptan groups (—SH groups) on the —$SO_3H$ group modified metal oxide catalyst. The general procedure used is as follows.

(2-Trihydroxysilyl)propanesulfonic acid (30% solution in water) was taken into water and added to a metal oxide in a 100 ml round bottom flask. Water was evaporated from the resulting mixture with stirring. The resulting solid residue was dried at about 130° C. for about 8 to 10 hours under vacuum to provide the sulfonic acid group functionalized metal oxide catalyst. To this was added an ethanolic solution of (3-mercaptopropyl)triethoxysilane (3-MPTS). Excess ethanol was then removed under vacuum, and the residual solid material was dried at about 130° C. for about 8 to 10 hours under vacuum to provide the desired catalyst.

Table 2 shows the weights of various starting materials used for preparing the silica-supported and zirconia-supported functionalized metal oxide catalysts.

TABLE 2

| Ex. | Functionalized Metal Oxide catalyst | trihydroxysilane propane sulfonic acid (30% solution in water) (ml) | Water (ml) | Metal Oxide (g) | 3-mercaptopropyltriethoxy silane (g) | Ethanol (ml) | Ethanolic solution of 3-mercaptopropyltriethoxy silane (ml) | Metal oxide functionalized with Sulfonic acid group |
|---|---|---|---|---|---|---|---|---|
| 4 | Functionalized Zirconia. | 3.6 | 10 | 5 Zirconia | 2.86 | 7.1 | 2 | 6.5 |
| 5 | Functionalized silica. | 3.6 | 10 | 5 silica | 2.86 | 7.1 | 2 | 6.5 |

Examples 6-7. These examples are directed to batch reactions of cyclohexanone with ortho-cresol in the presence of a catalyst system as indicated in Table 3 below. All of these reactions were carried out at a reaction temperature of about 75° C. In both examples, a molar ratio of cyclohexanone:ortho-cresol::1:25 was used. The weight percent catalyst loading was 5%. HPLC analysis was used to analyze the reaction mixtures with the weight percent of 1,1-bis(3-methyl-4-hyxdroyxphenyl)cyclohexane (DMBPC) obtained directly from the HPLC analysis. Results are shown in Table 3.

TABLE 3

Cyclohexane:ortho-cresol :: 1:25; Temperature: 75° C.; Catalyst loading: 5 weight %

| Example | Catalyst system | Time in hours | DMBPC selectivity weight % (Gurram to provide) |
|---|---|---|---|
| 6 | 20% HPA SiO$_2$ | 6 | 74.3 |
| | | 22.5 | 71.9 |
| | | 29 | 69.4 |
| | | 46.5 | 63.1 |
| | | 52.5 | 61.3 |
| | | 70 | 54.5 |
| | | 78 | 50.4 |
| 7 | Functionalized zirconia | 6 | 11.9 |
| | | 22.5 | 27.5 |
| | | 29 | 34 |
| | | 46.5 | 44.1 |
| | | 52.5 | 46.6 |
| | | 70 | 52.2 |
| | | 78 | 53.6 |

Example 8: This example is directed to a batch reaction of cyclohexanone with ortho-cresol in the presence of the functionalized silica catalyst system (as prepared in example 5) as indicated in Table 4 below. All of these reactions were carried out at a reaction temperature of about 65° C. The molar ratio of cyclohexanone:ortho-cresol::1:25 was used. The weight percent catalyst loading was 5%. HPLC analysis was used to analyze the reaction mixtures with the weight percent of 1,1-bus(3-methyl-4-hyxdroyxphenyl)cyclohexane (DMBPC) obtained directly from the HPLC analysis. Results are shown in Table 4.

TABLE 4

Cyclohexane:ortho-cresol :: 1:25; Temperature: 65° C.; Catalyst loading: 5 weight %

| Example | Catalyst system | Time (hours) | DMBPC selectivity (wt %) |
|---|---|---|---|
| 8 | Functionalized silica | 3 | 93.1 |
| | | 7 | 93.1 |
| | | 20 | 93.9 |
| | | 24 | 94.3 |
| | | 29 | 94.3 |
| | | 50 | 93.9 |
| | | 63 | 93.7 |
| | | 94 | 92.9 |

Comparative Example 1. This example is directed to a batch reaction of cyclohexanone with ortho-cresol in the presence of an ion exchange resin catalyst system with a promoter (Amberlite-15 with 3,500 ppm resorcinol as promoter) as indicated in Table 5 below. This reaction was carried out at a reaction temperature of about 65° C. The molar ratio of cylcohexanone:ortho-cresol::1:25 was used. The weight percent catalyst loading was 5%. HPLC analysis was used to analyze the reaction mixtures with the weight percent of 1,1-bis(3-mehtyl-4-hydroyxphenyl)cyclohexane (DMBPC) obtained directly from the HPLC analysis. Results are shown in Table 5.

TABLE 5

Cyclohexane:ortho-cresol :: 1:25; Temperature: 65° C.; Catalyst loading: 5 weight %

| Comparative Example 1 | Catalyst system | Time in hours | DMBPC selectivity weight % |
|---|---|---|---|
| | Amberlit-15 with 3500 ppm resorcinol | 7 | 88.2 |
| | | 11 | 89.2 |
| | | 21 | 91.2 |
| | | 24 | 89.8 |

Examples 9-10. These examples are directed to batch reactions of limonene with phenol in the presence of catalyst system as indicated in the Table 6 below. The examples have been carried out at a molar ratio of phenol:limonene::25:1 and the weight percent catalyst loading was 2% (except where indicated otherwise). The reaction temperatures are indicated in the Table 6 below. HPLC was used to analyze the reaction mixtures with the weight percent of BHPM obtained directly from the HPLC analysis. Results are shown in Table 6 below.

TABLE 6

Molar ratio of phenol:limonene::25:1; Catalyst loading 2 weight %

| Ex. | Catalyst system | Temp (° C.) | Time (hours) | 1,3-BHPM selectivity (wt %) | 2,8-BHPM selectivity (wt %) | 1,3-Trans BHPM selectivity (wt %) | Total selectivity (wt %) |
|---|---|---|---|---|---|---|---|
| 9 | Functionalized zirconia | 80 | 6 | UD | UD | UD | UD |
|   |   |   | 22 | 0.43 | 1.01 | UD | UD |
| 10 | Functionalized zirconia | 100 | 6.5 | 8.59 | 8.09 | UD | UD |
|   |   |   | 22 | 13.84 | 21.3 | UD | UD |
|   |   |   | 29.5 | 13.13 | 21.91 | UD | UD |
|   |   |   | 45 | 13.96 | 22.92 | UD | UD |

UD undetectable limits

Comparative Examples 2-3. These examples are directed to batch reactions of limonene with phenol in the presence of ion-exchange resin as indicated in the Table 5 below. The examples have been carried out at a molar ratio of phenol: limonene::25:1 (except as indicated otherwise) and the weight percent catalyst loading was 2%. The reaction temperatures used are indicated in the Table 7 below. HPLC was used to analyze the reaction mixtures with the weight percent of BHPM obtained directly from the HPLC analysis. Results are shown in Table 7 below.

TABLE 7

Molar ratio of phenol:limonene::25:1; Catalyst loading 2 weight %

| Comp. Ex. | Catalyst system | Temp. (° C.) | Time (hours) | 1,3-BHPM selectivity (wt %) | 2,8-BHPM selectivity (wt %) | 1,3-Trans BHPM selectivity (wt %) | Total weight selectivity (wt %) |
|---|---|---|---|---|---|---|---|
| 2 | Amberlite-15 | 40 (4 hours) | 8 | 26.33 | 14.08 | 8.41 | 40.41 |
|   |   | 100 (26 hours) | 10.5 | 29.13 | 15.09 | 9.73 | 44.21 |
|   |   |   | 22.5 | 30.12 | 16.25 | 12.01 | 46.37 |
| 3 | Amberlite-15 (phenol:limonene::25:1) | 40 (4 hours) | 10.5 | 14.241 | 2.43 | 4.44 | 36.67 |
|   |   | 100 (26 hours) | 22.5 | 3.272 | 21.65 | 5.79 | 34.92 |

It is observed from Examples 6-10 that catalyst systems like heteropolyacid, clay, and functionalized metal oxide catalysts are effective in the reaction of forming a bisphenol from an alkylating agent having a functionality of two and an aromatic hydroxy compound. However, it should be noted that the experiments conducted as part of this study were not optimized in all cases. Thus, it is believed that much higher yields than those shown in Tables 3, 4, and 6 are achievable for the disclosed catalyst systems, by adjusting various reaction parameters which are known to those skilled in the art. Such optimization falls within the scope of the disclosure.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A process for preparing aromatic bisphenols, the process comprising:
reacting an aromatic hydroxy compound with an alkylating agent having a functionality of two in the presence of a catalyst system, wherein the catalyst system is selected from the group consisting of a heteropolyacid compound, a clay, and a functionalized metal oxide catalyst, and wherein the alkylating agent having the functionality of two comprises a carbonyl compound of formula (I):

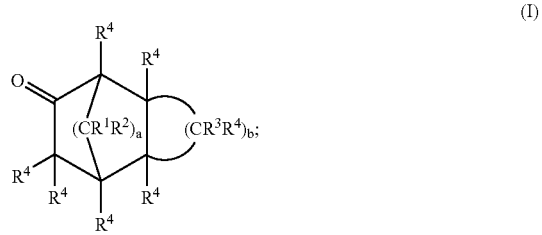

wherein $R^1$ to $R^4$ independently at each occurrence represent a hydrogen or an aliphatic radical, and "a" and "b" are integers independently having values from 0 to 3.

2. The process of claim 1, wherein the alkylating agent having the functionality of two is a cycloalkanone selected from the group consisting of substituted and unsubstituted tricyclo[5.2.1.0$^{2,6}$] decanones, cyclohexanone, 4-perhydrocumyl cyclohexanone, 3,3,5-trimethylcyclohexanone, and mixtures of the foregoing cycloalkanones.

3. The process of claim 1, wherein the heteropolyacid compound comprises a compound of formula (II):

$$(M^1)_3(M^2)(M^3)_{12}O_{40} \cdot yH_2O \quad (II);$$

wherein $M^1$ comprises hydrogen, or an alkali metal selected from the group consisting of lithium, sodium, potassium, rubidium, and cesium; $M^2$ comprises phosphorus or silicon, $M^3$ comprises tungsten or molybdenum, and "y" is an integer having a value 0 to 10.

4. The process of claim 1, wherein the heteropolyacid compound comprises at least one heteropolyacid metal salt selected from the group consisting of lithium, sodium, potassium, rubidium, and cesium salts, or mixtures of the foregoing salts.

5. The process of claim 1, wherein the heteropolyacid compound comprises at least one heteropolyacid selected from the group consisting of silicotungstic acid, silicomolybdic acid, phosphotungstic acid, and phosphomolybdic acid.

6. The process of claim 1, wherein the heteropolyacid compound comprises a compound of formula (III):

$$(M^4)(M^5)(M^6)_{12}O_{40} \cdot yH_2O \quad (III);$$

wherein $M^4$ comprises a Group III element; $M^5$ comprises phosphorus or silicon, $M^6$ comprises tungsten or molybdenum, and "y" is an integer having a value 0 to 10.

7. The process of claim 1, wherein the heteropolyacid compound is phosphotungstic acid.

8. The process of claim 1, wherein the clay is selected from the group consisting of:

$Al_4Si_8O_{20}(OH)_4$, $(M^7)_n{}^{x/n} \cdot aH_2O$ $(Al_{4-x} Mg_x)$ $Si_8 O_{20}$ $OH_4$;

$(M^7)_n{}^{x/n} \cdot aH_2O$ $Al_4$ $(Si_{8-x} \cdot Al_x)$ $O_{20}$ $OH_4$; $K_2 Al_4$ $(Si_6 Al_2)$ $O_{20}$ $OH_4$;

$Mg_6 Si_8 O_{20} OH_4$; $(M^7)_n{}^{x/n} \cdot aH_2O$ $(Mg_{6-x} Li_x)$ $Si_8 O_{20} (OH)_4$;

$(M^7)_n{}^{x/n} \cdot aH_2O$ $Mg_6 (Si_{8-x} Al_x) O_{20} OH_4$ and $K_2 Mg_6 Si_6 Al_2 OH_4$;

wherein $M^7$ comprises an alkali metal or an alkaline earth metal cation, and a, x, y, and n are integers.

9. The process of claim 8, wherein $M^7$ is selected from the group consisting of sodium or lithium.

10. The process of claim 1, wherein the clay is montmorillonite.

11. The process of claim 1, wherein the functionalized metal oxide catalyst consists essentially of structural units of the formulae,

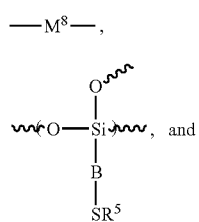

and

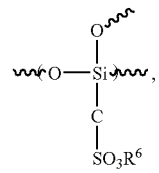

wherein $M^8$ comprises a metal oxide of a Group III element, a Group IV element, or combinations of the foregoing; "B" and "C" independently comprise spacer groups selected from the group consisting of an aliphatic radical, a cycloaliphatic radical and an aromatic radical; and $R^5$ and $R^6$ independently comprise an alkali metal, a hydrogen, or an aliphatic radical.

12. The process of claim 11, wherein the Group III element is selected from the group consisting of boron, aluminum, gallium, and combinations of the foregoing Group III elements.

13. The process of claim 11, wherein the Group IV element is selected from the group consisting of silicon, titanium, zirconium, and combination of the foregoing Group IV elements.

14. The process of claim 1, wherein the aromatic hydroxy compound is selected from the group consisting of phenol, ortho-cresol, meta-cresol, para-cresol, 2,6-xylenol, and mixtures of the foregoing aromatic hydroxy compounds.

15. The process of claim 1, wherein reacting the aromatic hydroxy compound and the alkylating agent having the functionality of two in the presence of the catalyst system comprises a batch, a semi-batch, or a continuous mode.

16. The process of claim 1, wherein reacting the aromatic hydroxy compound with the alkylating agent having the functionality of two in the presence of the catalyst system comprises a reaction temperature from 40° C. to 120° C.

17. The process of claim 1, wherein reacting the aromatic hydroxy compound with the alkylating agent having the functionality of two in the presence of the catalyst system comprises a mole ratio of the aromatic hydroxy compound to the carbonyl compound of 2:1 to 40:1.

18. The process of claim 1, wherein the catalyst system is 0.5 weight percent to 10 weight percent of an overall weight of the reaction mixture.

19. A process for making polycarbonate comprising reacting the aromatic bisphenols prepared according to the process of claim 1 with a carbonate precursor.

20. A process for preparing 1,1-bis(3-methyl-4-hyxdroxyphenyl)cyclohexane, wherein the method comprises reacting cyclohexanone with ortho-cresol in the presence of a catalyst system, wherein the catalyst system is selected from the group consisting of a heteropolyacid compound, a clay, and a functionalized metal oxide catalyst.

21. The process of claim 20, wherein reacting the cyclohexanone with the ortho-cresol in the presence of the catalyst system is at a temperature from 40° C. to 120° C.

22. The process of claim 20, wherein reacting the cyclohexanone with the ortho-cresol in the presence of the catalyst system comprises a mole ratio of ortho-cresol to cyclohexanone of 2:1 to 40:1.

23. The process of claim 20, wherein the catalyst system is 0.5 weight percent to 10 weight percent of an overall weight of the reaction mixture.

24. A process for preparing aromatic bisphenols, the process comprising:

reacting an aromatic hydroxy compound with an alkylating agent having a functionality of two in the presence of a catalyst system, wherein the catalyst system comprises a functionalized metal oxide catalyst; and wherein the alkylating agent having the functionality of two comprises at least one functional group selected from the group consisting of a cyclopropyl ring, a cyclobutyl ring, an ethylenic group, an aliphatic hydroxy group, and a cycloaliphatic hydroxy group.

25. The process of claim 24, wherein the alkylating agent having the functionality of two comprises a terpene compound.

26. The process of claim 25, wherein the terpene compound is selected from the group consisting of alpha-terpinene, alpha-terpinol, alpha-pinene, limonene, gamma-terpinene, alpha-pinene, beta-pinene, sabinene, 2-carene, 3-carene and mixtures of the foregoing terpene compounds.

27. The process of claim 25, wherein the functionalized metal oxide catalyst consists essentially of structural units of the formulae,

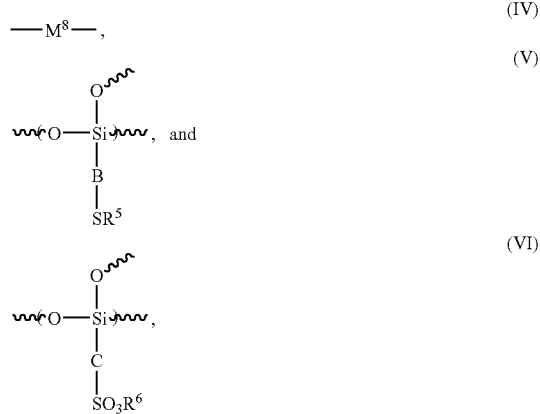

wherein $M^8$ comprises a metal oxide of a Group III element, a Group IV element, or combinations of the foregoing; "B" and "C" independently comprise spacer groups selected from the group consisting of an aliphatic radical, a cycloaliphatic radical and an aromatic radical; and $R^5$ and $R^6$ independently comprise an alkali metal, a hydrogen, or an aliphatic radical.

28. The process of claim 27, wherein the Group III element is selected from the group consisting of boron, aluminum, gallium, and combinations of the foregoing Group III elements.

29. The process of claim 27, wherein the Group IV element is selected from the group consisting of silicon, titanium, zirconium, and combination of the foregoing Group IV elements.

30. The process of claim 24, wherein the aromatic hydroxy compound is selected from the group consisting of phenol, ortho-cresol, meta-cresol, para-cresol, 2,6-xylenol, and mixtures of the foregoing aromatic hydroxy compounds.

31. The process of claim 24, wherein reacting the aromatic hydroxy compound and the alkylating agent having the functionality of two in the presence of the catalyst system comprises a batch, a semi-batch, or a continuous mode.

32. The process of claim 24, wherein reacting the aromatic hydroxy compound with the alkylating agent having the functionality of two in the presence of the catalyst system comprises a reaction temperature from 40° C. to 120° C.

33. The process of claim 24, wherein reacting the aromatic hydroxy compound with the alkylating agent having the functionality of two in the presence of the catalyst system comprises a mole ratio of the aromatic hydroxy compound to the carbonyl compound of 2:1 to 40:1.

34. The process of claim 24, wherein the catalyst system is 0.5 weight percent to 10 weight percent of an overall weight of the reaction mixture.

35. A process for making polycarbonate comprising reacting the aromatic bisphenols prepared according to the process of claim 24 with a carbonate precursor.

36. A process for preparing 1,3- and 2,8-bis(4-hydroxyphenyl)menthane, wherein the method comprises reacting limonene with phenol in the presence of a catalyst system, wherein the catalyst system comprises a functionalized metal oxide catalyst.

37. The process of claim 36, wherein reacting the limonene with the phenol in the presence of the catalyst system is at a temperature from 40° C. to 120° C.

38. The process of claim 36, wherein reacting the limonene with the phenol in the presence of the catalyst system comprises a ratio of phenol to limonene of 2:1 to 40:1.

39. The process of claim 36, wherein the catalyst system is 0.5 weight percent to 10 weight percent of an overall weight of the reaction mixture.

* * * * *